United States Patent [19]

Gorbach et al.

[11] Patent Number: 4,839,281
[45] Date of Patent: Jun. 13, 1989

[54] LACTOBACILLUS STRAINS AND METHODS OF SELECTION

[75] Inventors: Sherwood L. Gorbach, Chestnut Hill; Barry R. Goldin, W. Newton, both of Mass.

[73] Assignee: New England Medical Center Hospitals, Inc., Boston, Mass.

[21] Appl. No.: 724,114

[22] Filed: Apr. 17, 1985

[51] Int. Cl.$^4$ .......................... C12Q 1/04; C12N 1/36; C12N 1/20; C12R 1/225
[52] U.S. Cl. ................................ 435/34; 435/245; 435/252.9; 435/853; 435/854; 424/93
[58] Field of Search ...................... 435/29, 30, 34, 38, 435/245, 253, 854, 252.9, 853; 424/93

[56] References Cited

U.S. PATENT DOCUMENTS

4,689,226  8/1987  Nurmi et al. ........................ 426/2

FOREIGN PATENT DOCUMENTS

424402      7/1967   Australia ............................ 435/34
81300077.5  8/1981   European Pat. Off. ............ 435/253
1208599    10/1967   United Kingdom ................ 435/253
1167196    10/1969   United Kingdom ................ 435/253

OTHER PUBLICATIONS

Gilliand, et al., "Enumeration and Identity of Lactobacilli in Dietary Products"; *Biological Abstracts*, vol. 65, No. 6, (1978); Abstract No.: 34231.
Fuller, R.; "Epithelial Attachment and Other Factors Controlling the Colonization of the Intestine of the Grotobiotic Chicken by Lactobarilli"; *Biol. Abst.*, V. 67, No. 9; Abst. 54781, (1979).
Mayra–Makinen, A. et al.; "The Adherence of Lactic Acid Bacteria to the Columnar Epithelial Cells of Pigs and Calves"; *J. Appl. Bact.*, V. 55, (1983); pp. 241–245.
*The American Heritage Dictionary*, 2d ed., p. 145 (1982).
Klaenhammer (1985) J. Dairy Sci. 65:1339–49.
Kleeman et al. (1985), J. Dairy Sci. 65:2063–69.
Deneke et al. (1983), Infection and Immunity 39, 1102.

*Primary Examiner*—Elizabeth C. Weimar

[57] ABSTRACT

A biologically pure culture of a strain of bacteria of a Lactobacillus species in which the bacteria have avid adherence to intestinal cells, are able to survive at low pH, and produce large amounts of lactic acid.

6 Claims, No Drawings

LACTOBACILLUS STRAINS AND METHODS OF SELECTION

BACKGROUND OF THE INVENTION

This invention relates to therapeutically beneficial strains of bacteria, and particularly to strains of *Lactobacillus acidophilus*.

*L. acidophilus* is a component of the normal intestinal flora of most healthy human beings. The genus Lactobacillus is widely distributed in nature. Many species, such as *L. bulgaricus* and *L. casei*, are found in dairy products, as well as in fruits and vegetables. Other Lactobacillus species are encountered in the intestinal tract of mammals and insects. For many centuries, lactobacilli have been used in milk and dairy products as fermentation organisms, producing yogurt and various types of fermented and soured milks, curds and creams. The species of Lactobacillus used in the dairy industry is generally *L. bulgaricus*, although *L. acidophilus* strains have been used fairly extensively as well.

In recent years a number of studies have been carried out using *L. acidophilus* strains isolated at North Carolina State University ("NCSU"). These studies have yielded evidence that the NCSU strains, when ingested by humans or animals, produce beneficial effects on various functions of the gastrointestinal tract, including the suppression of activation of chemical carcinogens in the large bowel, a reduction of fecal excretion of cholesterol (related to a reduced risk of large bowel cancer), and a reduction of gastrointestinal side effects of antibiotic therapy.

SUMMARY OF THE INVENTION

The present invention features new *L. acidophilus* strains which exhibit a number of characteristics which render them beneficial to human health, and in particular render them useful in the treatment of the side effects of antibiotic therapy, ulcerative colitis, and constipation; in providing resistance to gastrointestinal colonization by pathogenic microorganisms and yeasts; in reducing fecal cholesterol excretion; and in reducing fecal estrogen excretion.

The *L. acidophilus* strains of the invention are characterized in that an average of at least 50, more preferably at least 100, of the bacteria can adhere to one human small intestinal mucosal cell after a five minute incubation of the bacteria with the cells. Preferably, the bacteria are further characterized in that they produce at least 3.5 milliequivalents ("meq") of lactic acid per $10^{10}$ CFU (colony forming units) in nutrient medium at 37° C. per day; they are capable of proliferating at 37° C. in nutrient medium at a pH value of 3.0; they are capable of proliferating in nutrient medium containing 0.1% oxgall bile; and they exhibit a generation time of less than one hour in nutrient medium at 37° C. ("Nutrient medium" refers to any culture medium containing the nutrients required for the proliferation of *L. acidophilus* bacteria.)

The invention also provides a method for isolating strains of the invention from a sample containing a multiplicity of bacterial strains, involving carrying out, in any order, the screening steps of isolating bacteria of the species *L. acidophilus*, and associating the bacteria with gastrointestinal cells and selecting bacteria capable of adhering to the cells at a rate of an average of at least 50, and more preferably at least 100, bacterial cells per gastrointestinal cell in a five minute coincubation period. Preferably the selection method also includes the steps of incubating bacteria of the sample in nutrient medium at a pH value below 5.5 (more preferably below 3.5) and selecting bacteria which proliferate in that medium; incubating bacteria of the sample in nutrient medium containing at least 0.1% bile and selecting bacteria which proliferate in that medium; and incubating bacteria of the sample with nutrient medium and selecting bacteria having a generation time of less than one hour at about 37° C.

Other features and advantages of the invention will be apparent from the following description of preferred embodiments thereof, and from the claims.

DESCRIPTION OF THE PREFERRED EMBODIMENTS

Strain Isolation

Healthy human beings carry bacteria of the species *L. acidophilus* as part of their normal flora, generally in concentrations of about $10^9$ lactobacilli per gram of intestinal contents; thus a healthy individual harbors in excess of $10^{11}$ lactobacilli in his intestinal tract. The first step in the method is to screen fecal specimens from humans and select those in which high lactobacillus concentrations are present.

Next, these samples are screened using a procedure designed to isolate strains exhibiting the characteristics discussed in the Summary of the Invention, above, and which can briefly be summarized as:

(1) Stability to acid
(2) Stability to bile (a property previously identified as desirable by the Department of Food Science, North Carolina State University)
(3) Ability to attach avidly to mucosal cells of the human intestinal tract
(4) Lactic acid production
(5) Hardy in vitro growth.

Stability to Acid and Bile

Screening for stability to bile, and for stability to a somewhat acidic environment, is accomplished as follows. LBS agar (described in J. Bacteriol. (1951) 62, 132) is prepared, having the following composition, per liter:

Triptycose and Peptone: 10.0 g
Yeast Extract: 5.0 g
Ammonium Citrate: 2.0 g
Monopotassium Phosphate: 6.0 g
Dextrose: 20.0 g
Polysorbate PO$_4$: 1.0 g
Sodium Acetate Hydrate: 25.0 g
Magnesium Sulfate: 0.575 g
Manganese Sulfate: 0.12 g
Ferrous Sulfate: 0.034 g
Agar: 15.0 g To 84 grams of powder of the above composition, dehydrated, are added 300 ml of tomato juice and 800 ml distilled water and, following mixing, 1.32 ml acetic acid. 1.5 g oxgall bile is then added, and the pH adjusted to 5.5 using 1N HCl. Plates are stored in an anaerobic chamber 1-3 days prior to use and then used without autoclaving. Fecal specimens from healthy individuals are homogenized in water, under anaerobic conditions, and serial dilutions incubated on the plates for 48 hours in an anaerobic chamber. The bacteria which proliferate on the plates are selected and screened further. This step eliminates many of the microorganisms in the sample.

Screening for stability to more acidic conditions is carried out using MRS broth (Difco; described in J. Applied Bacteriol. (1960) 23, 130), of the composition:
  Bacto Protease Peptone #3: 10.0 g
  Bacto Beef Extract: 10.0 g
  Bacto-Yeast Extract: 5.0 g
  Dextrose: 20.0 g
  Tween 80: 1.0 g
  Ammonium citrate: 2.0 g
  Sodium acetate: 5.0 g
  Magnesium sulfate: 0.1 g
  Manganese sulfate: 0.05 g
  Disodium phosphate: 2.0 g 55 g of powder of the above composition, dehydrated, is mixed with 1000 ml distilled water and sterilized by autoclaving for 15 min. at 15 lb. The broth has a final pH value of 6.5 at 25° C. The pH is then adjusted using 1.0N HCl and, if necessary, 1.0N NaOH, and the broth filter sterilized. Bacteria are incubated in the broth for 48 hours in an anaerobic chamber. Selected bacteria preferably can proliferate at pH below 3.5, preferably at pH 3.0.

L. acidophilus Selection

The next screening step is the isolation, from the bacteria able to proliferate in acid and bile, of bacteria of the species *L. acidophilus*. This step is carried out using standard microbiological techniques.

Adherence

The next step is to test acid and bile-stable *L. acidophilus* bacteria for the ability to adhere to gastrointestinal cells. Human gastrointestinal cells are first isolated, by any convenient method. One technique involves the collection of the effluent from a patient with a well functioning ileostomy by saline lavage.

The saline effluent is collected in cold 1/10 volume buffer I (0.1% gelatin, 1% glucose, 500 mM sodium phosphate, pH 7.4). This solution is then filtered through #25 silk to remove clumps and debris and the small intestinal (ileal) mucosal cells collected by centrifugation at $100 \times g$ for 10 min. The cells are then washed in buffer II (0.45% NaCl, 0.1% glucose, 0.01% gelatin, 50 mM sodium phosphate, pH 7.4) using the same centrifuge conditions. Finally, the cells are resuspended in buffer II, ⅓ volume of tissue culture medium NCTC 135 is added, and the cells are stored at 4° C. until use. Ileal cell number and viability are determined by Trypan Blue staining. The human ileal cells can be frozen in liquid nitrogen after the addition of 10% (v/v) glycerol.

The bacteria are grown for 18 hours at 37° C. in MRS broth with 6 $\mu$Ci of $^3$H alanine and $^3$H-leucine added. The bacteria are then washed in 5 volumes of phosphate buffered saline, resuspended in buffer II, and filtered through 2.0$\mu$ polycarbonate filters to remove clumps. The bacteria are then mixed with the human small intestinal cells, incubated at 37° C., and samples taken 5 minutes later. The samples are placed on 2.0$\mu$ polycarbonate filters and the excess liquid removed by gentle suction. The filters are then rinsed, first with 2 ml then with 5 ml of phosphate buffered saline (pH 7.4). Using these filters the ileal cells and attached bacteria are retained but the free bacteria pass through. Controls include the reaction mixture without the human small intestinal cells. The radioactivity retained is determined by liquid scintillation. The bacterial specific activity is determined from the colony forming units calculated from the optical density at 550 nm and the radioactivity retained by 0.2$\mu$ filters. The bacterial specific activity is used to calculate the numbers of bacteria bound.

Bacteria which bind, according to the above procedure, at a rate of at least 50, and more preferably 100, bacteria per gastrointestinal cell (representing approximately 10% of the bacteria contacted with the cells) are the desired bacteria.

Lactic Acid Production

Lactic acid production is measured by incubating bacteria in MRS broth or Scott Peptone Yeast Broth under anaerobic conditions and measuring lactic acid at 8 or 24 hours using gas liquid chromatography. Selected bacteria produce at least 3.5 meq, and more preferably over 4 meq, of lactic acid per $10^{10}$ CFU at 37° C. in a 24 hour period.

Hardy Growth

The final screening step is the selection of bacteria which exhibit hardy growth in vitro, as measured by generation time. $5 \times 10^4$ CFU of bacteria are used to inoculate nutrient medium, e.g., MRS broth, and CFU measured at 1, 2, 3, 4, 5, 6, 7, and 8 hours by plating 0.1 ml of diluted aliquots onto LBS agar and incubating plates for 48 hours at 37° C. under anaerobic conditions. Bacteria are selected which have a generation time, at 37° C., of less than one hour, more preferably about 45 minutes.

Screening Rationale

Each step in the above screening procedure is designed to isolate *L. acidophilus* strains possessing characteristics which render them capable of enhancing human health.

Acid and bile stability are important because the bacteria are ingested and must pass through the acidic environment of the stomach as well as the bile containing small intestine, and they must be able to survive and proliferate under these conditions if the bacteria are to confer health benefits on the person ingesting them.

Adherence is important because this property permits the *L. acidophilus* bacteria to colonize and become established in the gastrointestinal tract.

Lactic acid production is important because it is believed that the lactic acid produced by the bacteria is in part responsible for the beneficial effects of colonization of the gastrointestinal tract by the strains of the invention. Lactic acid is an antimicrobial substance, and its production by the strains of the invention can help them form a protective barrier to pathogens within the gastrointestinal tract. Lactic acid may also aid in the inactivation of carcinogens in the gastrointestinal tract.

Hardy in vitro growth is an important property because the strains of the invention must be produced on a large scale; hardy growth is also an indicator that the bacteria will likely grow well in vivo as well.

Characteristics of Strain GG

One strain of the invention, designated GG, has the following characteristic.

Acid Stability

The GG strain can grow at pH 3.0 up to a concentration of $1 \times 10^7$ CFU. At higher pH's the growth is even higher, achieving $10^9$ CFU at pH 5.0.

In normal human gastric juice, the GG strain, starting at an inoculum of $10^8$ CFU, can survive, with less than 2 log decline in inoculum size, for at least 30 minutes at pH 2.5.

Bacteria of the G strain ($10^9$ CFU) were inoculated down a Levine tube directly into the stomach of a healthy volunteer. With gastric contents at pH 1.0–2.0, at least 1,000 organisms of the GG strain survived for a minimum of two hours.

Bile stability

The GG strain could grow in oxgall bile at a concentration of 0.15% in LBS agar.

Adherence to Intestinal Mucosal Cells

The table below shows the extent of adherence of bacteria of the GG strain to ileal mucosal cells.

| TIME OF EXPOSURE | NO. OF BACTERIA BOUND PER INTESTINAL CELL |
| --- | --- |
| 5 minutes | 119 |
| 10 minutes | 235 |
| 15 minutes | 333 |

Lactic Acid Production

The production of lactic acid was measured by gas liquid chromatography, following incubation of the GG strain in liquid nutrient broth. The following lactic acid concentrations were measured, at the given times of incubation.

| TIME OF INCUBATION | LACTIC ACID PRODUCTION |
| --- | --- |
| 8 hours | 1.53 meq/$10^8$ CFU |
| 24 hours | 4.44 meq/$10^{10}$ CFU |

Generation Time

The GG strain exhibited hardy growth in vitro. using an initial inoculum of $5 \times 10^4$ CFU in MRS broth, the strain showed a 40 fold increase in growth during a four hour period, reaching a density of $2 \times 10^6$ CFU. Thus, during this four hour period there were 5.2 generations, giving a single generation time of 45 minutes.

Use

The L. acidophilus strains of the invention can be cultured on a large scale and used therapeutically, in lypholized form or in conjunction with a pharmaceutically acceptable carrier substance, and can be added to food products, particularly dairy products such as milk and yogurt, as has been done with other L. acidophilus strains for many years. The bacteria of the strains, alone, in food, or in other carrier vehicles, can be taken orally by a human patient, in an effective amount (e.g., $10^6$–$10^{10}$ bacteria per person per day) to treat or prevent a variety of medical disorders, mentioned above and now discussed in more detail. Culture conditions are as follows.

A stock solution consists of sterile skim milk containing $10^{10}$ CFU viable organisms. 1 ml of this stock solution is added to 2 liters of MRS broth. The vessel is placed in an anaerobic incubation chamber and grown overnight for 14 hours with general stirring at 37° C. The broth is centrifuged at 10,000×g for 20 minutes, and the pellet is resuspended in 50–100 ml of sterile skim milk and stored at 80° C.

In one particular mode of administration, $10^9$ to $10^{10}$ organisms are added to milk, either in volumes of 10 to 20 ml, or larger volumes, e.g., 250 to 500 ml. The milk is administered once daily, so that $10^9$ to $10^{10}$ CFU are given in a single administration. For animals, 0.2 to 1.0 ml of the stock milk solution is mixed into their food, so that they receive $10^9$ to $10^{10}$ CFU of the bacteria daily.

Side Effects of Antibiotic Therapy

Diarrhea is the major complication of antibiotic treatment, occurring in approximately 10% of patients receiving antibiotics, particularly ampicillin, amoxacillin, cephalosporins, clindamycin, erythromycin, and tetracyclines. The strains of the invention can be used to treat antibiotic induced diarrhea, in the same manner that other L. acidophilus preparations have been used in the past. In addition, the strains can be used, prior to or concurrently with antibiotic therapy, as a prophylaxis. Such prophylactic administration should occur within 24 hours of the antibiotic therapy.

Ulcerative Colitis

Idiopathic ulcerative colitis, also known as inflammatory bowel disease, represents a difficult therapeutic problem. The disease is rather common, and patients suffer recurrent attacks of diarrhea, which can appear on multiple occasions over years of active disease. At the present time the only therapies that have proven successful are salicylazosulfapyridine (SAS) and corticosteroids. Many patients relapse despite these treatments. In addition, the treatments themselves are associated with a high incidence of side effects.

Several lines of evidence have suggested that the intestinal microflora is involved in this disease process, either as an initiator or as a determinant of symptoms.

Bacteria of the L. acidophilus strains of the invention can be administered, as described above for antibiotic side effects, to treat or prevent ulcerative colitis.

Constipation

Sluggish bowel action and chronic constipation are major problems in older people. Constipation leads to abdominal distention, cramps, and general malaise. The interest of the general public in promoting good bowel activity is reflected in the panoply of products available in the drugstore for alleviating this condition. These products vary from harsh laxatives, to short chain fatty acids, to various natural fiber products, such as pectins, lignins, gums, and mucilages.

Cultured dairy products, yogurts, and soured milks have been employed throughout history to aid chronic constipation.

Bacteria of the L. acidophilus strains of the invention can be employed alone, as described above, or can be admixed with a sub therapeutic dose of lactulose, a synthetic disaccharide which has been used to treat constipation. The lactulose will be metabolized by the bacteria, enhancing their beneficial effect without producing the side effects which are sometimes associated with therapeutic doses of lactulose.

Colonization Resistance

It has become apparent in recent years that colonization of the gastrointestinal tract in humans provides a reservoir for dissemination of pathogenic microorganisms, especially in immunocompromised hosts. The intestinal microflora of healthy individuals can resist implantation of undesirable microorganisms through a number of internal control mechanisms. While these control mechanisms are poorly understood, the net result is relative stability of the human intestinal flora, with maintenance of the same types and same concentrations of bacteria over long periods of time.

Through the impact of antibiotic treatment, undesirable microorganisms are able to colonize the gastrointestinal tract. Among the bacteria, these undesirable organisms include Pseudomonas, Enterobacter, Serratia, Klebsiella, Citrobacter and Proteus Providencia. Fungi can also colonize the gut, especially yeasts such as Candida.

While healthy individuals can withstand intestinal colonization even during antibiotic treatment, immunocompromised hosts face a serious threat in this circumstance. These undesirable microorganisms can invade the mucosa, producing septicemia and life-threatening illness.

The clinical settings in which intestinal colonization with undesirable microorganisms become important include cancer, especially in those patients treated with potent chemotherapy; inherited or acquired immunodeficiency syndromes; patients treated with corticosteroids for a variety of conditions; and recipients of organ transplants such as kidney, bone marrow, heart, and liver. There are also elderly, debilitated patients who are colonized and eventually infected by these undesirable microorganisms. Among infants, admission to intensive care units often is associated with antibiotic treatment, poor nutritional status, and immunocompromising conditions. This group of high-risk children is also challenged by the problems of colonization with potentially pathogenic bacteria and yeasts.

Maintenance of the natural resistance to overgrowth by undesirable microorganisms is known in the recent scientific literature by the term "colonization resistance" (CR). Various ploys have been undertaken to either enhance colonization resistance or, alternatively, prevent overgrowth by intestinal microorganisms. Enhancement of CR is achieved by using antibiotics that produce only minimal effects in the composition of the normal intestinal flora, especially by maintaining the normal anaerobic components that seem to be responsible for resisting overgrowth by undesirable microorganisms. The alternative method is prevention of colonization by administering oral antibiotics that essentially kill off any new entrants into the microflora. This method produces a "sterile" microflora, at least for short periods of time.

While each of these methods to prevent colonization has certain attractions, they are not necessarily effective. Relatively few therapeutic antibiotics are able to maintain the CR, so this ploy is often unsuccessful. The other method involving administration of oral antibiotics produces many side effects of its own, and it is often unsuccessful since highly resistant microorganisms may colonize even in the presence of antimicrobial drugs. Thus, the problems of colonization by undesirable microorganisms in immunocompromised hosts, whether adults or children, remains a major problem in modern medicine.

Bacteria of the *L. acidophilus* strains of the invention can be administered to patients, as described above, to provide CR in a benign way, since the bacteria have no intrinsic pathogenicity. Colonization of the intestine by this natural organism could prevent other pathogenic forms from entering the flora, while at the same time maintaining a relatively healthy intestinal environment.

Cholesterol Excretion

Considerable interest has been aroused in recent years in the fecal excretion of sterols, particularly cholesterol, since there may be a correlation with colon cancer. Studies in experimental animals, carried out over a decade ago, showed that chemically induced colon cancer could be augmented by increased excretion of cholesterol in the feces.

It has been known for some time that cholesterol undergoes an enterohepatic circulation, resulting in intestinal reabsorption of some cholesterol and fecal excretion of the remainder. Within the large intestine cholesterol is subjected to microbial reduction to coprostanol and coprostanone. Most individuals excrete the majority of cholesterol as these reduced end products, but approximately 20% of people excrete mostly pure cholesterol, with only small amounts of the reduction products.

While these animal studies were interesting, their relevance was not held to be significant, until clinical trials on cholesterol lowering drugs were published. These studies showed that the cholesterol-lowering drugs, such as atromid, were successful in reducing serum cholesterol levels and in reducing heart attacks. The corollary, however, was an increase in large bowel cancer, for the lowering of serum cholesterol came at the expense of increasing fecal cholesterol. These clinical trials verified the results seen in animals, whereby higher levels of fecal cholesterol were associated with increased risk of colon cancer.

Bacteria of the *L. acidophilus* strains of the invention can be administered to patients, as described above, to reduce the amount of cholesterol excreted in the patients' feces.

Estrogen Excretion

Improvements in laboratory techniques for measuring estrogens have widened our understanding of these important sex hormones. Estrogens are produced largely in the ovaries and, to a lesser extent, in fat and other tissues. The major excretion of estrogens are via the urine.

An important development in recent years is understanding the enterohepatic circulation of estrogens. It has been shown that as much as half of circulating estrogens are recycled throughout the bile into the intestinal tract, where they are reabsorbed into the body. Only 5% of estrogens are excreted in the feces.

In order to be excreted in the bile, estrogens are conjugated, generally as a glucuruonide or sulfonate. These conjugated estrogens pass through the bile into the intestinal tract, where they are deconjugated by intestinal bacteria and subsequently reabsorbed.

The importance of the enterohepatic circulation was shown in studies by Adlercreutz et al., in which fecal and urinary estrogens were tested in women receiving ampicillin for a minor infection. This oral antibiotic caused a 30% reduction in excretion of urinary estrogens, with a concomitant increase in fecal estrogen excretion. The explanation is that the antibiotic suppressed bacteria within the intestine responsible for deconjugating the estrogens. This led to decreased intestinal reabsorption, and increased fecal excretion of estrogens.

Many studies have established that higher estrogen levels in urine and plasma are correlated with increased risk of breast cancer. This appears to fit with the observation that vegetarian women, having lower levels of urine and plasma estrogens, have reduced rates of breast cancer.

Bacteria of the L. acidophilus strains of the invention can be administered, as described above, to menstruating women to lower the amount of excreted estrogen; the same deconjugating enzymes involved in estrogen reabsorption are influenced by ingestion of L. acidophilus.

Deposits

The GG strain of L. acidophilus has been deposited in the American Type Culture Collection, Rockville, Mass., and has been given ATCC Accession No. Applicants' assignee, New England Medical Center Hospitals, Inc., acknowledges its responsibility to replace these cultures should they die before the end of the term of a patent issued hereon, and its responsibility to notify the ATCC of the issuance of such a patent, at which time the deposits will be made available to the public. Until this time the deposits will be made available to the Commissioner of Patents under the terms of 37 CFR §1.14 and 35 USC §112.

Other embodiments are within the following claims.

We claim:

1. A biologically pure culture of bacteria of a Lactobacillus species, said bacteria being characterized in that they have the same ability to attach mucosal cells of the human intestinal tract as that exhibited by the Lactobacillus bacteria deposited in the American Type Culture Collection and given ATCC Accession No. 53103.

2. The culture of claim 1, having ATCC Accession No. 53103.

3. A method of isolating a therapeutically useful strain of a Lactobacillus species, said method comprising carrying out the following screening steps on a sample containing a multiplicity of bacterial strains:
    (a) isolating from said sample bacteria of a Lactobacillus species,
    (b) coincubating bacteria of said sample with gastrointestinal cells, and
    (c) selecting bacteria capable of adhering to said cells at a rate of an average of at least 50 bacterial cells per gastrointestinal cell in five minutes of coincubation.

Lactobacillus species bacteria capable of so adhering comprising said therapeutically useful strain.

4. The method of claim 3, further comprising the step of incubating bacterial of said sample in nutrient medium at a pH below 5.5 and selecting bacteria which proliferate in said medium.

5. The method of claim 3 further comprising the step of incubating bacteria of said sample in nutrient medium containing at least 0.1% bile and selecting bacteria which proliferate in said medium.

6. A biologically pure culture of bacteria of a Lactobacillus species, wherein said culture is selected by the process of claim 3.

* * * * *